United States Patent [19]

Dittmann et al.

[11] Patent Number: 5,239,376
[45] Date of Patent: Aug. 24, 1993

[54] WEB DEFECT CONTINUOUS SURVEILLANCE SYSTEM

[75] Inventors: Randall L. Dittmann, Duluth; Scott B. Petersen, Proctor; William L. Bundschuh, Duluth, all of Minn.

[73] Assignee: Lake Superior Paper Industries, Duluth, Minn.

[21] Appl. No.: 843,356

[22] Filed: Feb. 11, 1992

[51] Int. Cl.⁵ .............................................. H04N 7/18
[52] U.S. Cl. .................................... 358/101; 358/106; 358/108
[58] Field of Search ............... 358/101, 108, 106, 107, 358/22, 183

[56] References Cited

U.S. PATENT DOCUMENTS

| | | | |
|---|---|---|---|
| 4,172,264 | 10/1979 | Taylor | 358/183 |
| 4,337,482 | 6/1982 | Coutta | 358/108 |
| 4,481,533 | 11/1984 | Alzmann | 358/101 |
| 4,519,041 | 5/1985 | Fant et al. | 364/552 |
| 4,583,181 | 4/1986 | Gerber et al. | 358/106 |
| 4,675,730 | 6/1987 | Adomaitis et al. | 358/106 |
| 4,737,846 | 4/1988 | Tokuno et al. | 358/106 |
| 4,794,453 | 12/1988 | Gnuechtel et al. | 358/101 |
| 4,805,019 | 2/1989 | Holliday | 358/107 |
| 4,941,660 | 7/1990 | Winn | 358/22 |
| 4,955,720 | 9/1990 | Blecha et al. | 356/429 |
| 5,023,714 | 6/1991 | Lemelson | 358/107 |

Primary Examiner—Tommy Chin
Assistant Examiner—Richard Lee
Attorney, Agent, or Firm—Haugen and Nikolai

[57] ABSTRACT

A video surveillance system for monitoring a continuous web of material negotiating the tortuous path through a paper making machine employs a plurality of video cameras for the continuous monitoring of the web arranged in pairs, each pair addressing a different location of interest along the paper making path. All of the cameras are operated using a single external sync signal and produce video output signals which, in turn, are fed to a plurality of video image splitters, each splitting the video output from a pair of cameras. Video recorders are provided for recording and playing back the split video output signals from each video image splitter through video monitors. The system is computer controlled and responsive to input signals indicative of web failure.

7 Claims, 4 Drawing Sheets

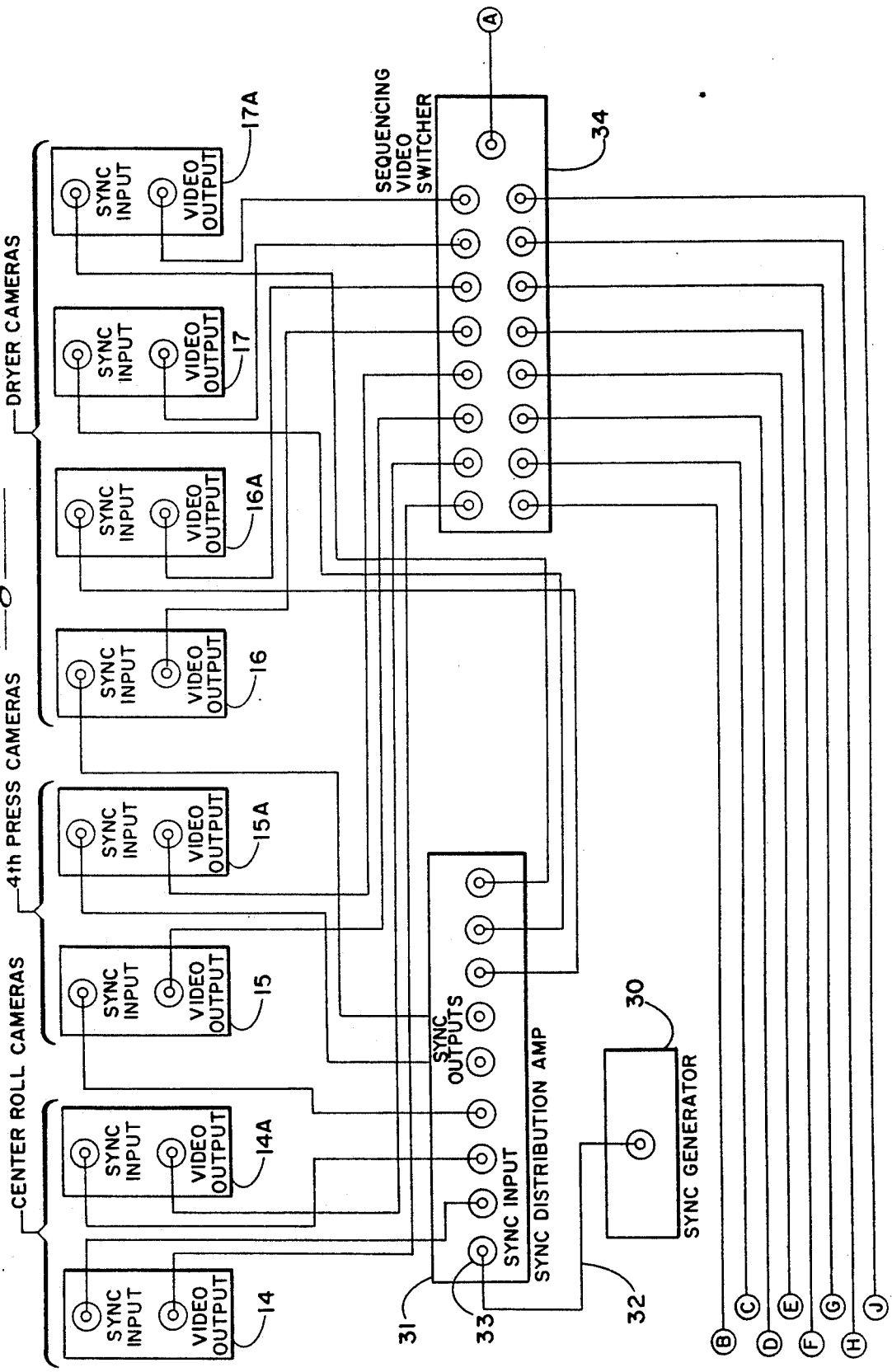

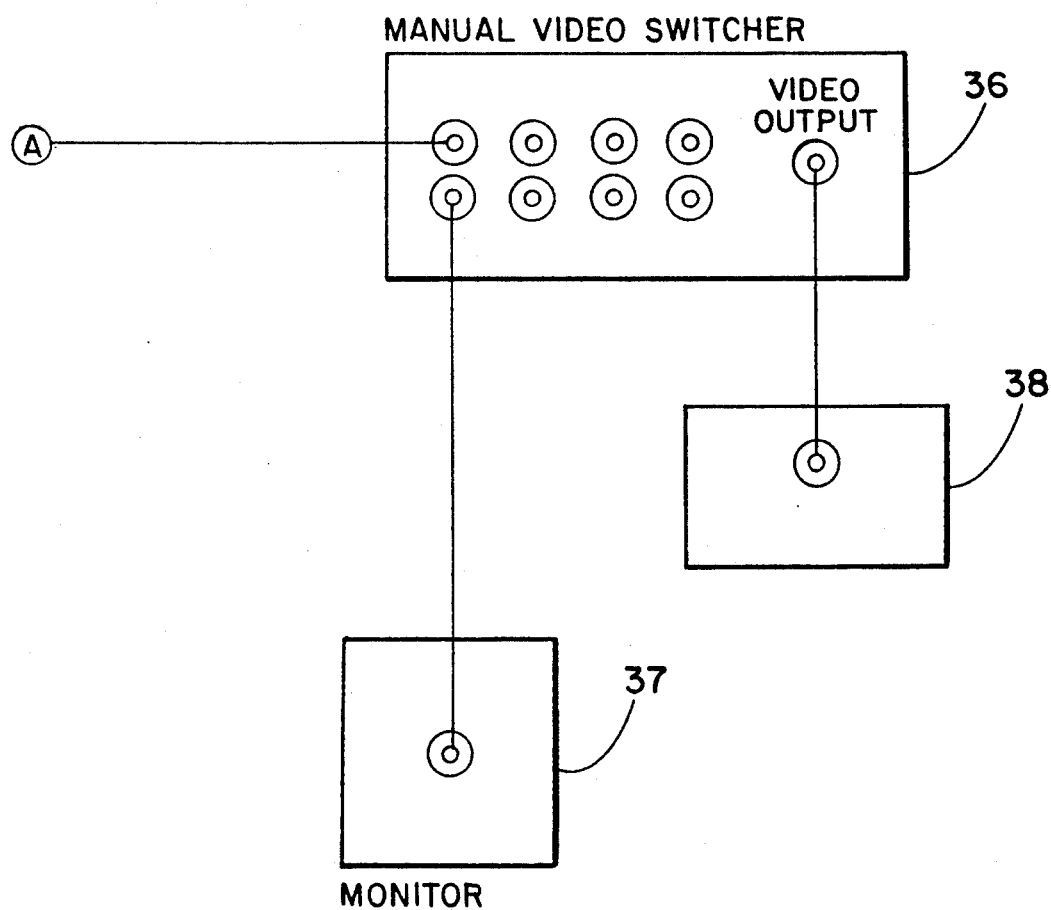

WEB DEFECT CONTINUOUS SURVEILLANCE SYSTEM

BACKGROUND OF THE INVENTION

I. Field of the Invention

This invention is directed generally to a video surveillance system for monitoring a continuous web, such as a web of paper navigating through the many rolls of a paper machine from the head box at the wet end or formation section to the dry end. More particularly, the invention relates to an integrated video surveillance system using multiple cameras and multiple video screens to display, record and playback the operation at critical points in the machine such that, upon the occurrence of a failure or break in the web, the system can automatically or manually replay events recorded just prior to the break to aid in determining the cause of the web failure.

II. Description of the Related Art

The making of paper includes the passing of a long, continuous web of material over a plurality of rolls in continuous form. The web is formed from a heated slurry of bleached pulp fibers, starch, clay and other additives containing about one part bleached fibers and additives combined with 99 parts water. The slurry is received as furnish from the head box between two endless wire screens and formed into a relatively wide uniform sheet which is thereafter squeeze dried between a plurality of heavy rollers and eventually wound on reels in the form of large paper rolls which may be cut to any desired length and width. The continuous web may have a width approaching 25 feet and be many hundreds of feet long. The forming process utilizes both heat and pressure to form a relatively thick, slow moving mass into what may be a very thin layer of dry paper moving at high speed as it is wound on large spindles at the exit end of the paper machine. During this process, the continuous web encompasses a variety of types of rollers and tension control devices. These include initial heated drying drums, drum rollers, thickness reduction rollers, and, in the case of high-gloss papers, super calender rollers which "iron" the paper between hard steel rollers and roller covers with more resilient coverings.

It is apparent that a process where a continuous web of material such as paper is being processed as a single continuous length of material beginning at its formation from a slurry through its polished, highly finished condition in roll form, the integrity of the web is critical to the continued operation of the process. Because defects and imperfections in the web do occur from time to time, and because such devices as those controlling web tension, for example, sometimes get out of calibration, web failures occur. In addition, with the exception of the very beginning of a formation of the paper web in the wet end of the paper machine, the web itself moves quite rapidly such that by the time the dried web of final thickness is reached, the speed of the web of material moving through the process is extremely rapid, reaching as much as 100 feet per second. Thus, when a break in the web does occur, it happens very rapidly and, even if viewed in real-time, the cause often is not apparent. Thereafter it may be extremely difficult to determine the exact cause of the web failure. While devices exist which monitor the continuity of the continuous web and which operate to shut down the machinery quickly should breakage or discontinuity occur, such devices do not aid in determining the cause of web failure.

Systems for inspecting and characterizing continuous webs of material later for defects including providing video recordings of the passage of a continuous web of materials such as paper are known. One such system records the passage of a continuous web of paper on videotape which can subsequently be replayed and inspected thereby allowing inspection of the material to be carried out separately from the real-time material processing. This system is disclosed in Wales et al. (U.S. Pat. No. 4,951,223). Another monitoring system is shown in Pajunan (U.S. Pat. No. 4,918,422). Further multi-camera video surveillance systems are disclosed in Oliver, Jr. (U.S. Pat. No. 4,814,869) and Williams (U.S. Pat. 4,581,634).

Each time the paper web fails, the paper making machine must be stopped while the cause of the breakage is determined, any necessary equipment repairs made and the continuous web rethreaded so that the machine can resume operation. Such "down time" is very expensive as the entire process comes to a standstill. Minimizing down time is a very important consideration in any such continuous operation. Early diagnosis of the cause of the breakage or failure may be critical with respect to the time it takes to conduct any necessary repairs and restore the line to full operation. Therefore, a system which enables the operator to determine the cause of the failure more rapidly could provide invaluable information with respect to conducting any necessary repairs.

A surveillance system which can monitor the continuous web of a paper making machine in a manner such that when breaks occur, the interval just prior to the break can be automatically replayed to determine the probable cause of the web failure has remained a definite need with respect to the operation of paper machines. It would be a great advantage to have a multi-camera surveillance system which could react to breaks in the continuous paper web in a manner which would facilitate diagnosis of the cause of the web failure in a manner such that the cause can be diagnosed and the system corrected in the shortest possible time.

SUMMARY OF THE INVENTION

The present invention is directed to a surveillance system for monitoring the continuous web of a paper making machine in a manner such that continuous video surveillance of the operation of the machine from a plurality of locations or a continuous basis enables web breakage or failure to be recorded such that video information recorded prior to the break can be utilized to troubleshoot the cause of the break or web failure. The video surveillance system utilizes a plurality of pairs of coordinated cameras in a video freeway which monitor the most critical areas of the machine where breaks are most likely to occur. The video cameras operate in conjunction with a lesser number of real-time/time-lapsed video recorders and monitors. The system basically is made up of three sub-systems including a (1) video imaging system, (2) a synchronizing system, and (3) a recording and playback system.

One embodiment of the system uses eight video cameras in the form of four pairs of cameras mounted at the front and back sides of the paper making machine in strategic locations. Paired images from the cameras mounted on the front and back sides of a common location are brought into a split-screen configuration such that the eight cameras result in four pairs of split-screen images which can be displayed on four monitors and, at the same time, be recorded by four VCRs. The synchronization system includes a sync generator and a distribution amplifier which assures that all cameras, splitters, recorders and monitors receive the same source of synchronizing information so that the multiplexing of the system operates smoothly and with respect to the same sync signal. The eight paired images are recorded with four real-time/time-lapsed video recorders which are networked and driven with one personal computer. All four pair of images can be monitored in real-time with the four monitors which allows viewing of the recorded pairs of images also in a playback mode. A sequencing switcher is provided which receives input from all cameras and allows full screen playback of the output of any camera and the printing of individual frames by a printer also provided. The system is controlled and coordinated by a central processing unit (CPU) which may be a personal computer. The CPU also provides central sequential control of all four video recorders and individual control of a selected video recorder for playback. The computer also manages the logistics of tape rewinding, playing, etc., and generally oversees the status of all devices in the system.

In operation, the system continuously monitors the operation of the paper making machine and records the video or split-screen images continually, erasing and recording over on the tapes. The occurrence of a sheet failure is detected by a separate inspection system which operates in a well-known manner and provides a signal of the event to an input at the personal computer or other central processing unit. Upon receiving this alarm, the computer allows all video recorders to record for an additional period of time, possibly 15 seconds. After this has occurred, all recorders are instructed to stop and rewind for a set period of time, nominally 30 seconds of recorded tape, stop, pause and wait for instructions to begin playback. Playback of all eight images paired with the split-screen configuration can be viewed on the four video monitors simultaneously thereby allowing reinspection of the designated critical errors of the paper making machine with respect to occurrences just prior to the web failure or break. Selected images can be played back at a much slower speed and still images processed, if desired, to show the actual failure.

BRIEF DESCRIPTION OF THE DRAWINGS

In the drawings, wherein like numerals are utilized to designate like parts throughout the same:

FIGS. 2A, 2B and 2C represent a composite schematic diagram of the continuous web surveillance system of the invention.

DETAILED DESCRIPTION

During the manufacture of a moving web of paper, unlimited types of disruptions can occur which result in failure of the paper web and lost production. The use of video equipment to continuously monitor and record the web during manufacture can provide information imperative to troubleshooting numerous causes of paper web failures. Accordingly, the system of the present invention has been found to be invaluable with respect to reducing down time and minimizing lost production in a paper making machine. The following description will describe a particular paper web surveillance troubleshooting system but is meant to describe the invention by way of example only and by no means as a limitation on the possible embodiments utilizing the concepts of the invention.

Figure 1:
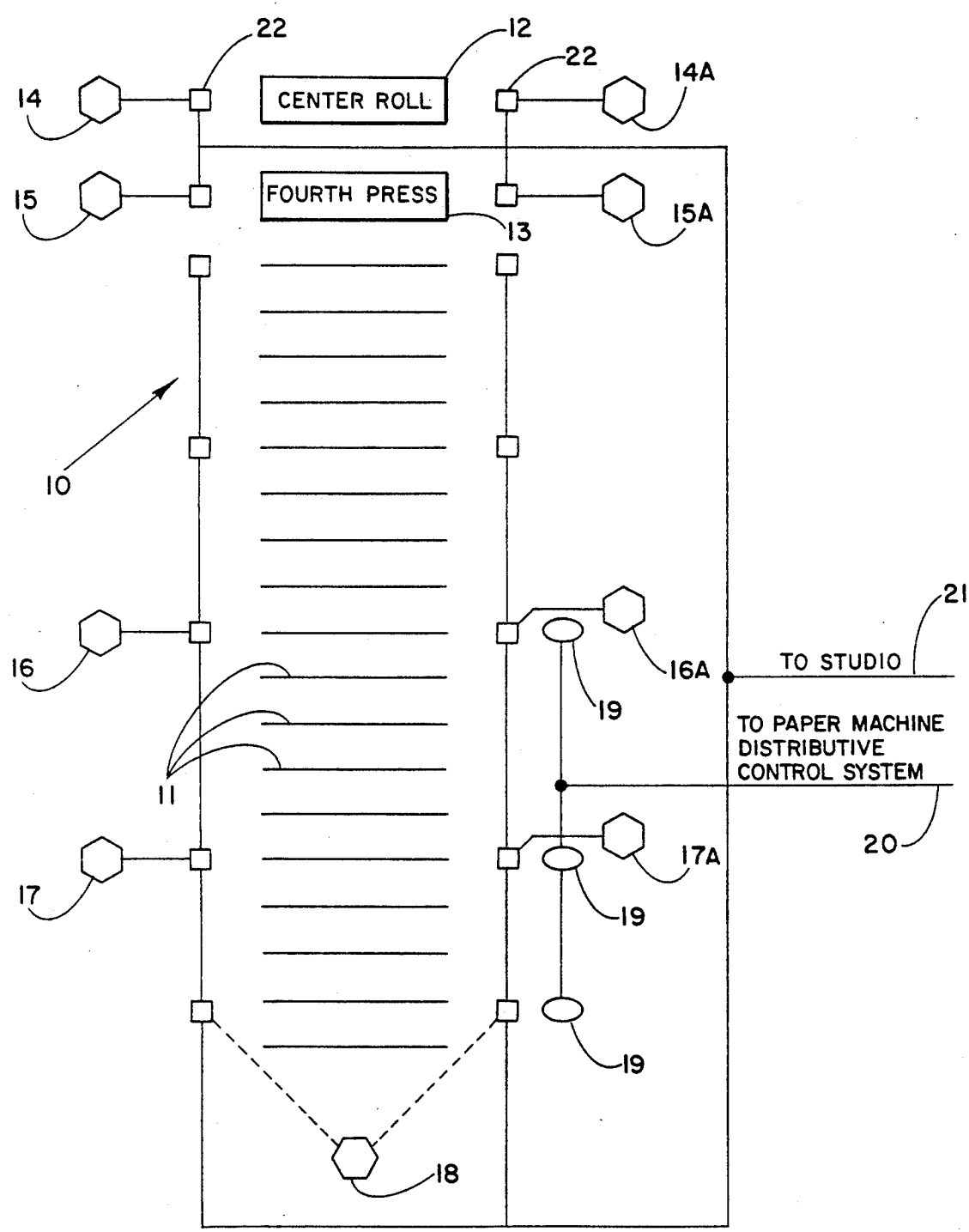
FIG. 1 is a schematic representation of a paper making machine including a possible configuration of surveillance camera and web failure detection device.

The schematic diagram of FIG. 1 depicts a schematic layout of a paper making machine in which the wet section or initial web forming portion of the machine is depicted at the top and the final finished paper section is at the bottom of the Figure. The machine depicted generally at 10 includes a plurality of presses and rolls 11 and includes an initial center roll 12 and a designated fourth press roll 13. Pairs of cameras 14 and 14A, 15 and 15A, 16 and 16A, and 17 and 17A are depicted at various strategic locations along the paper making machine. A further roving camera, not part of the system, is shown at 18. In addition, a plurality of sheet break decoders which check the continuity of the paper web in a well-known manner are shown at 19. They are connected to a paper machine distributive control system which monitors the continuity of the web as by conductor 20. Signals from the cameras are also shown collectively being conducted to the studio as by a conductive cable 21. While four pairs of cameras are shown in the system, it will be appreciated that any desired number can be utilized. The eight cameras represent a number of cameras which, when strategically mounted in pairs, cover the parts of the machine where breaks are most likely to occur.

Since the cameras are located close to the moving web and within the confines of the paper making machine itself, they are further exposed to the extreme conditions utilized in forming, rolling and drying the web. Thus, each camera must be protected from a hostile environment which may be typically 120° to 180° F. and 75% to 100% relative humidity. Therefore, each camera must be provided with a space-conditioned enclosure. Each camera unit is linked to one of 14 junction stations 22, which make up a video freeway. The 14 junction stations provide the eight cameras with 24 volt power for operation, high pressure air for camera cooling, or the like, as necessary for environmental adaptation, and a video or data transmission link which connects with the studio via conductor cable 21.

Figure 2B:
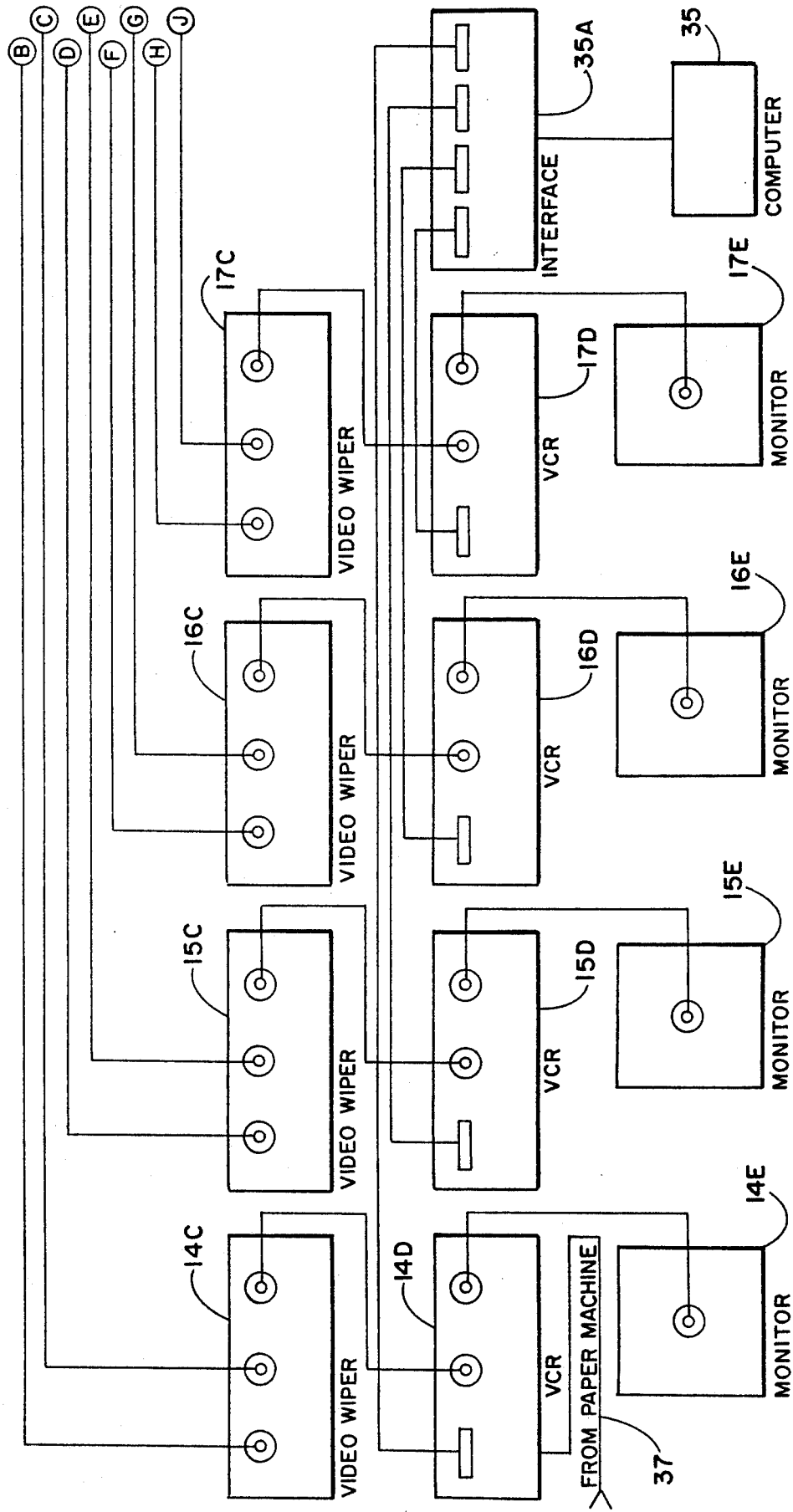

The remainder of the continuous web surveillance system is shown in FIGS. 2A-2C. This will next be described. As seen in the diagrammatic layout, the eight video cameras are synchronized with a sync generator 30 in conjunction with a sync distribution amplifier 31 (FIG. 2A). The sync generator produces a "black level" that is required by the cameras and video splitters to enable them to be "genlocked" together.

"Black level" is a term that is used to describe the horizontal blanking and sync pulses required for each line of picture information. Thus, at the start of each horizontal line of pixels of picture information, an horizontal "blanking" pulse is generated. This pulse which is also referred to as the pedestal level, has the "front porch", the horizontal sync pulse and the "back porch" riding on it.

The "black level", then, is the darkest part of a transmitted picture and is designed to operated at a given value, normally 0.3 volts above the sync pulse. When video equipment is set up for proper operation, the sync level is set to a value of 0.3 volts below the black level. As can be seen from the schematic diagram of FIG. 2A, the cameras used in the system of the invention have the capability of using an external sync source. In this manner, the sync generator 31 is connected via a cable 32 to a sync input 33 in the sync distribution amplifier. The sync distribution amplifier further has a series of outputs as shown connected to each of the cameras in the system. Thus, the video images produced are not dependent upon the individual internal sync generators that are present in each camera.

Likewise, the result of the use of this single signal sync system is that all cameras, video wipers, recorders and monitors receive the same source of sync information at the same time via the cameras. The black level generated by the system sync generator, then, is distributed throughout the system thereby ensuring a stable video picture at the monitors. In this manner, the distribution amplifier simply distributes the "genlocked" signal (black level) to all genlockable devices in the system at the proper level (in this case, 0.3 volts).

The video imaging system further includes a manual sequencing video switcher 34, video wipers or splitters 14C, 15C, 16C and 17C associated with the similarly numbered pair of cameras. These, in turn, are connected with similarly associated VCRs 14D, 15D, 16D and 17D and monitors 14E, 15E, 16E and 17E. A central processing unit (CPU) which may be a personal computer is shown at 35 connected to the system by a computer interface input/output device 35A (FIG. 2B); and other peripheral equipment shown in FIG. 2C includes a manual video switcher 36, shown connected to a monitor 37 which may be a separate monitor but which is nominally one of the monitors 14E, 15E, 16E or 17E utilized to show the output of any camera pair or a full image of a single camera of a pair but may be a separate monitor. In addition, an image copier or video printer 38 may be provided to produce replicas of displayed frames for analysis and archival purposes. This may produce 3×5 pictures, for example. Input 37 from the paper making machine distributive control center is shown coming into VCR 14D at 37. This connection is shown as a method of inputting information with regard to sheet failure at some point in the paper making machine.

In this manner, the video imaging system includes the cameras, the video wipers or splitters, a sequencing switcher, the video monitors and a video printer. Of course, since each camera is locked by the system sync generator and each pair of cameras is fed into a video splitter, the two individual images may be merged in one video screen and displayed. The personal computer 35 provides a central sequential control of all four video recorders 14D, 15D, 16D and 17D and individual control of a selected recorder as at 36 which may be used for playback analysis and printing. This, of course, allows an unlimited number of applications for automatic operation of the system and makes it flexible and readily adaptable to the application desired.

Generally, in operation, the cameras are started along with all recorders at sometime during the normal operation of the paper making machine, and all the recorders are operated in the record mode providing a continual monitoring of the machine.

When a sheet failure is detected by the separate sheet inspection system and the event is singled via input 37 and interconnects to the CPU or personal computer, upon receiving this alarm, the computer allows all video recorders to keep on recording for an additional period of time, possibly about 15 seconds. After this has occurred, all recorders are instructed to stop and reverse for a period of time greater than the additional run time, possibly 30 seconds. After this, the recorders are instructed to stop, pause and wait for the instruction to begin playing. Playback of all eight images paired with the split screen configuration can be viewed on the four video monitors simultaneously.

Backing up beyond the time of web breakage signal allows one to view events in the paper machine just prior to web breakage or failure. Playback can be made at any speed desired by the operator, for example, playback speeds can range from the normal two hour to a slow 180 hour set speed. In this mode, it is possible for the operator to view the sheet break from where it originated all the way through the machine, frame by frame. In addition, the feature can be utilized which allows the operator to review the tapes in a reverse mode at normal speed. This function combined with a pause and playback can enhance the ability of the operators to locate the exact point of interest on the tapes for study showing the break as it occurred. Of course, many other functions may be provided including automatic rewind of the tapes, signals for recorder problems, or the like. Manual/automatic control of all functions may be provided.

In this manner, the CPU or personal computer becomes the driver which also manages the logistics of the system including tape rewinding, playing, recording, etc., and can additionally be used to supervise the status of each device in the system as desired. For example, alarms may be provided for end of tape or lack of tape in a video recorder. In addition, other peripherals can be provided as needed.

The ability to review the critical period just prior to web failure at any desired speed provides the input necessary to evaluate the cause of the problem so that necessary adjustments and/or repairs can be started quickly and the machine restored to normal operation. If only a defect in the paper web is to blame, this, too, often will show up. In this manner, valuable time can be saved.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications both as to equipment and procedure details can be accomplished without departing from the scope of the invention itself.

We claim:

1. A video surveillance system for monitoring a continuous web of material navigating a paper making machine comprising:
   a plurality of video cameras for the continuous monitoring of the web arranged in pairs, each of said pairs addressing a different location of interest along the paper making machine, each of said cameras being adapted to receive and operate using an external sync signal and produce a video output signal;
   a plurality of video image splitters each of which is for splitting the video output signal from each said pair of cameras;
   a plurality of video recorders each of which is for recording and playing back the split video output signals from each of said video image splitters;

a plurality of video monitors each of which is for displaying a sequence of split-screen images from said each pair of video cameras;

synchronization means, including synchronization signal generating means for generating a synchronization signal for the operation of all the cameras;

means for receiving and responding to an independent alerting input signal indicating the occurrence of an event to be reviewed;

wherein the means for responding to the alerting input signal includes means for causing the cameras and recorders to cease operation after a predetermined time and rewind the videotape in the recorders to a point corresponding to a predetermined time before the alerting input signal was received so that the event can thereafter be immediately reviewed; and control means including computer means for controlling the operation of the system.

2. The video surveillance system of claim 1 wherein the event which needs to be reviewed is a failure of the continuous web.

3. The video surveillance system of claim 1 wherein the number of said pairs of video cameras is four.

4. The video surveillance system of claim 1 wherein the synchronization means further comprises:

a genlock sync generator for producing a genlock signal;

a distribution amplifier connected between the genlock sync generator and the plurality of video cameras for distributing the genlock signal to all said cameras in the system.

5. The video surveillance system of claim 1 further comprising video switching means for selectively viewing the output of said each camera as a full-screen image.

6. The video surveillance system of claim 5 further comprising a video printer means for printing a recorded video frame of interest from any said camera or pair of cameras.

7. A video surveillance system for monitoring a continuous web of material navigating a paper making machine comprising:

a plurality of video cameras for the continuous monitoring of the web arranged in pairs, each said pair addressing a different location of interest along the paper making machine, said each camera being adapted to receive and operate using an external sync signal and producing a video output signal;

a plurality of video image splitters for splitting the video output signal from said each pair of cameras;

a plurality of video recorders, one for recording and playing back the split video output signals from each of said video image splitters;

a plurality of video monitors for displaying a sequence of split-screen images from said each pair of video cameras;

synchronization means, including synchronization signal generating means for generating a synchronization signal for the operation of all the cameras;

means for receiving and responding to an independent alerting input signal indicating a failure of the paper web;

wherein the means for receiving and responding to the independent alerting input signal indicating a failure somewhere in the continuous web includes means for causing the cameras and recorders to cease operation after a predetermined time following receipt of the alerting input signal and rewind the recorders to a place corresponding to a point a predetermined time before the alerting input signal was received;

video switching means for selectively viewing the output of said each cameras as a full-screen image;

video printing means for printing a recorded video frame of interest from any said camera or pair of cameras; and control means including computer means for controlling the operation of the system.

* * * * *